United States Patent [19]

Perkins et al.

[11] Patent Number: 4,588,612
[45] Date of Patent: May 13, 1986

[54] PRETREATMENT IN ENCAPSULATION PROCESS

[75] Inventors: Douglas W. Perkins, Medina; Anthony V. Petricca, Rocky River, both of Ohio

[73] Assignee: SCM Corporation, New York, N.Y.

[21] Appl. No.: 726,408

[22] Filed: Apr. 24, 1985

[51] Int. Cl.<sup>4</sup> .............................................. B05D 1/22
[52] U.S. Cl. ..................... 427/213; 427/220; 426/307
[58] Field of Search ............... 427/213, 220; 426/307

[56] References Cited
U.S. PATENT DOCUMENTS

| 2,986,475 | 5/1961 | Mesnard et al. | 427/213 |
| 3,447,950 | 6/1969 | Evans et al. | 427/213 |
| 3,740,248 | 6/1973 | Buhler et al. | 427/220 X |
| 4,139,639 | 2/1979 | Bahoshy et al. | 426/3 |
| 4,384,004 | 5/1983 | Cea et al. | 426/3 |

Primary Examiner—Shrive P. Beck
Attorney, Agent, or Firm—Richard H. Thomas

[57] ABSTRACT

A process for encapsulating materials which are difficult to fluidize in a fluidized bed reactor comprising the steps of (1) compacting said materials into a plurality of flat chips; (2) grinding said chips into particles having a small particle size; (3) forming a fluid bed of the particles of step (2) in a fluid bed spray reactor; (4) applying a spray of a melted or molten hydrogenated liquid or wax to the surface of said particles in said reactor, encapsulating said particles; withdrawing said encapsulating material from said reactor.

6 Claims, 2 Drawing Figures

PRETREATMENT IN ENCAPSULATION PROCESS

The present invention relates broadly to fluid bed encapsulation, and more specifically to an encapsulation process in which the particles to be encapsulated are subjected to a preliminary compaction step. The present invention is particularly applicable to the encapsulation of particles which have a long, needle-like, crystalline structure, such as aspartame; and will be described in detail with reference to such particles, although it will be apparent to those skilled in the art that the present invention has other applications, such as the encapsulation of other difficult to encapsulate materials.

The present invention is particularly concerned with the preparation of coated aspartame particles suitable for food baking applications such as pre-mixes for cakes, sweet rolls, Danish rolls and cookies. Aspartame is very sensitive to high heat and an alkaline pH. It is one object of the present invention to provide a coated aspartame powder which is capable of resisting the adverse affects of these conditions.

BACKGROUND ART

Prior U.S. Pat. No. 4,139,639 to Bahoshy et al, describes encapsulating aspartame with gum arabic or dextrin using either spray drying or coacervation. In either process, the encapsulating material and aspartame are first formed into a water-based emulsion. The disclosure of this patent is remote from the concepts of the present invention.

It is known to encapsulate aspartame using a fluid bed-type process, as described in prior U.S. Pat. No. 4,384,004 to Cea et al. More specifically, the process employed in this patent is referred to as the Wurster process, and it is characterized as one that operates in a "similar fashion" to a fluidized bed coating process. Pretreatment for the aspartame, for instance pretreatment by compaction, is not disclosed or suggested in the patent. The coating material is described as a water soluble solution, dispersion or emulsion of a material like gum arabic, dextrin, cellulose derivatives, waxes, gelatin, zein and the like. Application is by finely atomizing the coating onto the aspartame particles.

Several "Wurster process" patents are referred to in the Cea et al patent. All appear to be somewhat different, and the Cea et al patent is not specific on which process is used. Reference is made to an Example II process in the above mentioned U.S. Pat. No. 4,139,639, but there is no Example II in this patent.

A commercially available form of the Wurster process or apparatus is one similar to FIG. 7 of Wurster U.S. Pat. No. 3,241,520. In this patent, a spouting bed is established within a cylindrical partition, with recirculation downwardly and back via an annulus around the partition. In large commercial units, a plurality of these cylindrical partitions and accompanying spray nozzles are employed. A spray nozzle is centered and positioned beneath the partion. Whereas this process and apparatus may function well with application of a water-soluble dextrin or gum arabic, or other solvent coating, to the aspartame, it is more difficult, for a number of reasons, for encapsulation by a melted hydrocarbon or wax, such as a partially hydrogenated vegetable oil stearine.

For one, the use of multiple spray nozzles in the larger production units to spray apply a melted hydrocarbon or wax into a fluid bed is impractical. Should one of the nozzles plug, this could occur without the operator knowing it, resulting in uneven application of coating.

Powders, such as aspartame, possess a needle-like crystal structure which causes them to "snowball" when placed in a conventional fluid bed reactor. In this phenomenon, the crystals tend to intertwine or cling together as they fluidize, causing the formation of soft, fibrous, aggregate balls of aspartame.

Although the crystals can easily be broken up with minimal direct mechanical pressure, the relatively gentle motion of the fluid bed induces the aggregates to grow unchecked, resulting in disruption of necessary fluid bed movement.

Traditionally, a fluidized bed reactor can be used to dry, granulate, or encapsulate solid particulate material. The particulate material must be free flowing in the bed before it can be effectively processed. Powders that exhibit poor flow characteristics can often be rendered acceptable for fluid bed processing by the addition of free-flow agents such as silicon dioxide, tricalcium phosphate, magnesium oxide, or a number of other agents. Occasionally, the added free-flow agents do not significantly improve particle flow.

In the present instance, this was the case. Particle flow properties of aspartame in a fluidized bed were not improved by the addition of various amounts of either silicon dioxide or dicalcium phosphate, two common free-flow agents. In addition, low bulk density starch bulking agents such as maltodextrin were unsuccessfully employed to improve the flow properties of aspartame in a fluid bed.

There are other crystalline products that in a natural state have a needle-like structure and, thus, as with aspartame, are difficult to encapsulate. One example is niacinamide, a nutritional supplement, which has the same detrimental flow characteristics as aspartame. Another example is Ibuprofen, an anti-inflammatory drug (Merck Index, Tenth Edition, Monograph 4797).

DISCLOSURE OF THE INVENTION

The above and other disadvantages are overcome, in accordance with the concepts of the present invention, by the improvement comprising compacting the needle-like crystals into a plurality of flat chips and then comminuting the chips to a small particle size prior to forming a fluidized bed of the crystals.

More specifically, the present invention resides in the method comprising the steps of; (1) compacting needle-like crystals into a plurality of flat chips; (2) grinding said chips to an average particle size in the range of about 20 to about 400 mesh, U.S. Standard Sieve; (3) forming a fluid bed of the chips of the particles of step (2) in a fluid bed spray reactor; (4) applying a spray of an encapsulating material to the surface of said particles in said reactor, encapsulating said particles, and (5) withdrawing the encapsulated material from said reactor.

Preferred encapsulating materials are molten or melted hydrogenated lipids and waxes.

In a preferred embodiment of the present invention, the crystals encapsulated are crystals of aspartame and the coating material is a stearine having a Wiley Melting Point in the range of about 120°–180° F.

BRIEF DESCRIPTION OF DRAWINGS

The present invention and advantages thereof will become more apparent upon consideration of the following specification, with reference to the accompanying drawings, in which.

Figure 1:
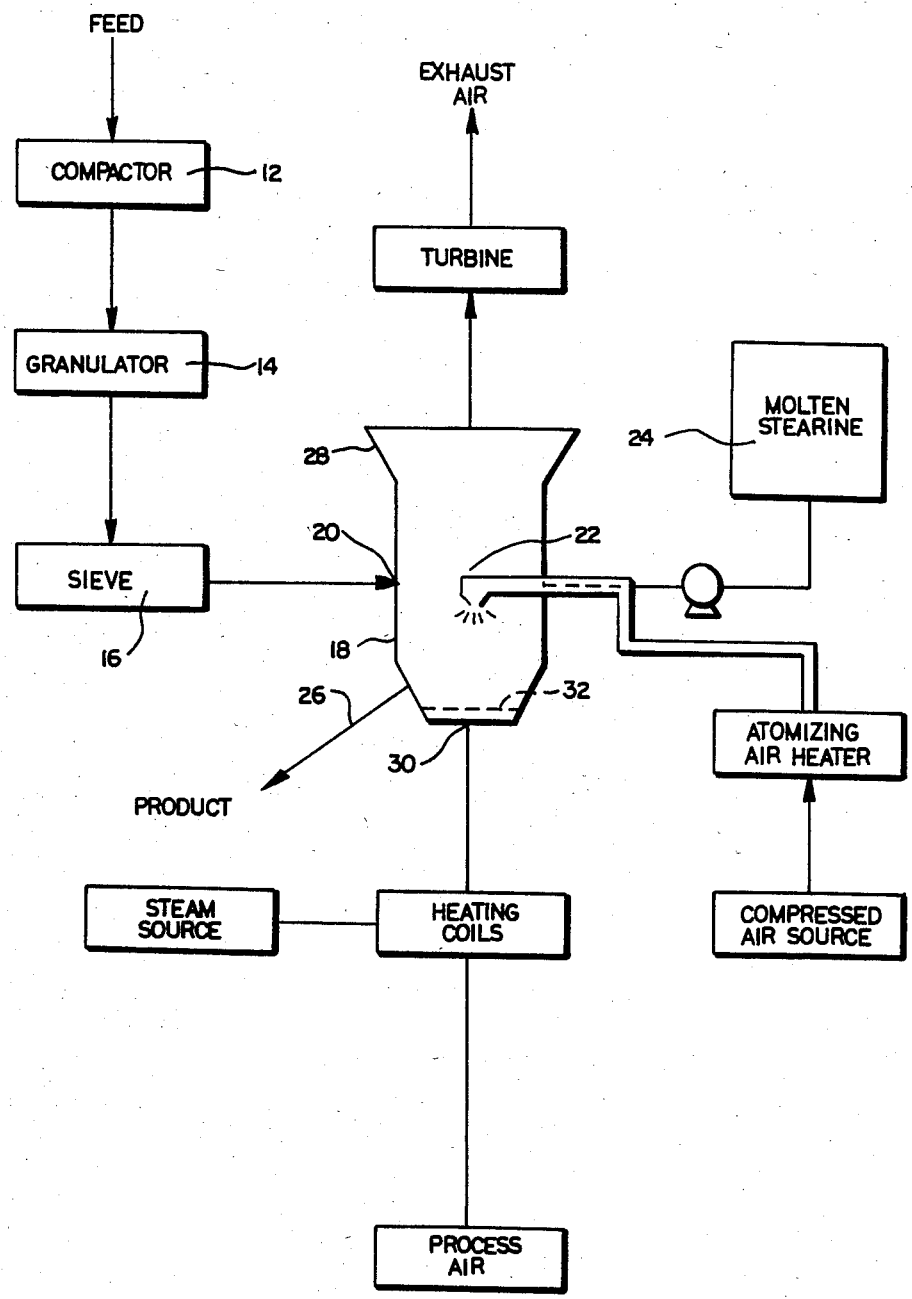
FIG. 1 is a schematic flow diagram illustrating the process of the present invention.

Referring to the drawings, and in particular FIG. 1, feed product which is aspartame, and which has a long needle-like, crystalline structure, is first fed to a compactor 12, the details of which will be described, which functions to compact the particles into a plurality of flat, disc-like chips. From the compactor, the chips are fed to a granulator 14, where the aspartame chips are comminuted into a desired particle sizing. Following granulation, the particles are then classified in a vibrating screen system 16, to obtain a product having a desired average particle size, for instance about 20 to about 80 mesh. The product of the screening is then fed to a fluidized bed reactor 18, the details of which also will be described.

In the reactor 18, the coating material, for instance a molten stearine, wax, or other hydrogenated vegetable oil, is sprayed onto the aspartame through nozzle 22 from tank 24 (wherein the coating material is maintained in a molten or heated condition). The processing is carried out on a batch basis, and at the end of encapsulation or coating, product is withdrawn via line 26.

The spray fluidized bed reactor 18 is a conventional or known piece of equipment, such as one marketed by Glatt Air Techniques, Inc., Model GPCG. A similar apparatus is marketed by Aeromatic, Inc. of Bernardsville, N.J., and also by Vector Freund.

Essentially, the apparatus comprises a closed chamber having an inlet 30 at the bottom of the chamber for introducing a fluidizing medium into the chamber. The lower part of the chamber is a product bowl limited or defined along the bottom by an air distribution plate 32, the inlet 20 for particulate material being positioned above the distribution plate, and also above the normal level of the particulate material in the fluid bed. The spray nozzle 22 is also positioned just above the normal level of the bed, as shown in FIG. 1, for spraying stearine or other coating material onto the bed. At the top of the chamber is an expansion zone 28 to limit the height of the bed, the area between the product bowl and expansion zone being characterized as the apparatus spray chamber.

In operation, the stearine or other composition in tank 24 is reduced to a melted, fluid state. The fluidizing medium, for instance air, introduced at inlet 30, is heated, the degree of heating depending upon the melting point of the coating material. The velocity of the fluidizing medium in the chamber 18 is that necessary to establish the fluid bed, and will be known to those skilled in the art.

The temperature and flow rate of the coating material and atomization pressure employed are dependent upon the equipment used in the manufacturer's specification. By way of example, a molten stearine, at about 120°–180° F., may be pumped through a binary nozzle e.g., manufactured by Schlick Co., having a port size of about 1.2–2.5 millimeters, at a flow rate of about 10 liters per minute, in a 500 kilogram production reactor.

The loading of particles in the fluid bed reactor is also dependent upon the manufacturer's specifications, and will be lower when a higher ratio of coating material to particulates is desired. By way of example, the loading of material to be coated in a 500 kilogram production granulator may be about 500–900 kilograms of particulate material for a product which is to be about 10% coating; and about 300–500 kilograms for preparation of a product which is intended to be about 50% coating.

Removal of product from the fluidized bed reactor is carried out when the desired concentration of stearine on the particulate substrate is reached.

Figure 2:
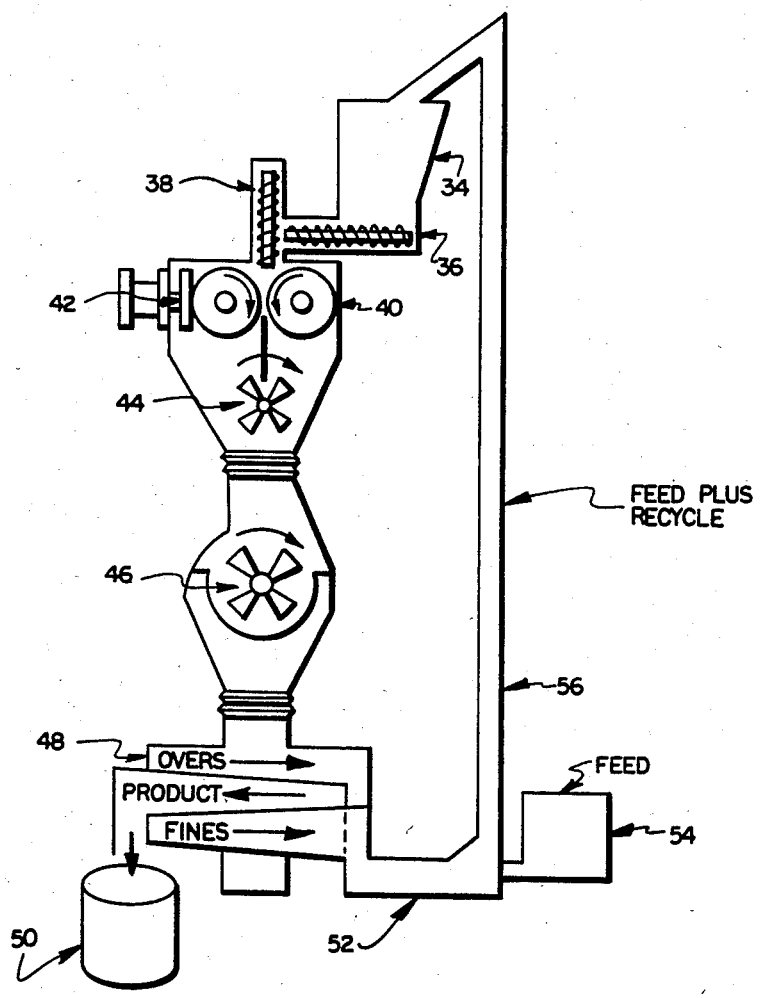
FIG. 2 is a schematic elevation view of a type of compactor/granulator that can be employed in the process of FIG. 1.

Turning to FIG. 2, material to be compacted is first fed into an upper feed hopper 34, from which it is forced by horizontal feed screw 36 into vertical screw 38, which pre-compresses and de-aerates the product. From the screw 38 the particulate material is dropped into the nip between grooved compression rolls 40. Hydraulic actuator 42 regulates the pressure exerted on the compaction rolls. Following compaction, the material is in ribbed sheet form, and drops onto pre-breaker 44, which breaks the sheets into chips and flakes. This material then flows downwardly into granulator 46, which breaks up the material into the desired particle sizes. From the granulator, the material flows, by gravity, to screen 48, which separates the particles into product 50 and recycle 52.

Initially, powder feed is introduced into lower hopper 54, and both feed and recycle are fed via recycle system 56 to the upper hopper 34.

An example of the type of equipment illustrated in FIG. 2 is a Chilsonator L-80, marketed and manufactured by the Fitzpatrick Co. The compaction rolls 40 are grooved so that the sheets passing from the grooved rolls are correspondingly grooved.

In the classification system, particles greater than a predetermined mesh are combined with those fines less than a different predetermined mesh, and recycled to compaction and grinding in recycle system 56. The finished product preferably is thus substantially between the two mesh sizes.

By the present invention, it was found that the particles, in the fluid bed reactor 18, move freely and independently, with no evidence of "snowballing", as had been observed with treatment of aspartame not subjected to the compaction/granulation pretreatment.

Microscopic examination of the particles following compaction/granulation revealed a non-needle-like structure.

The effectiveness of the present invention in protecting the aspartame through baking applications also has been observed. From prototypes tested, it has been determined that 50 to 75% recovery of aspartame unaffected by heat or alkalinity, following baking, is attainable.

The particular coating material used depends upon the end application contemplated. Although the coating material can be either water soluble or water insoluble, the present invention is principally useful with water insoluble coatings, suitable for premixes in the manufacture of baked goods such as cakes, sweet rolls, Danish rolls and cookies. The coating material should be normally solid at ambient temperatures, and more specifically, solid and nonsticky at temperatures up to about 90° F., and even higher. The coating should be capable of being melted at reasonable temperatures of application to the particulate substrate. For instance, in the case of aspartame, which is sensitive to high heat, the coating material should be meltable at temperatures in the range of about 140°–180° F. To provide good shelf life, the coating materials are preferably hydrogenated, and have low Iodine Values, for instance less than about 10.

An advantage of a fat coating for aspartame is believed to be that it effectively protects the aspartame from moist heat developed during baking.

An example of a hydrogenated vegetable oil particularly suitable for coating aspartame and providing a product useful in the preparation of cakes, is Durkee 17 (trademark, SCM Corporation) a partially hydrogenated soybean oil stearine. This composition is marketed in flake form, has an Iodine Value of about 4 max., and a Capillary Melting Point in the range of about 152°–158° F. The composition provides a non-sticky, hard surface at room to hot ambient temperatures (e.g., 78°–95° F.), has long shelf life, and provides good protection to the aspartame at normal baking temperatures, e.g., about 400°–500° F.

Examples of other suitable food grade hydrogenated oils, emulsifiers and waxes are given in the following Table:

| Composition | Trademark, if applicable | Properties |
|---|---|---|
| cottonseed oil stearine | Durkee 07* | CMP = 141–147° F. |
| | | IV = 4 max. |
| palm oil stearine | Durkee 27* | CMP = 136–144° F. |
| | | IV = 5 max. |
| mono- and diglyceride emulsifier | Durkee 117* | CMP = 140–150° F. |
| | | IV = 5 max. |
| partially hydrogenated vegetable oil hard butter | Paramount X* | WMP = 112–114° F. |
| paraffin wax | | MP = 50–57° F. |
| carnauba wax | | MP = 82–85.5° F. |
| | | IV = 13 |

*trademark SCM Corporation

EXAMPLE

In this Example, 33 pounds of aspartame powder were fed into a compaction unit 12, FIG. 1, identifiable as a Chilsonator (trademark Fitzpatricks Company), Model L-80. The compaction rolls 40, FIG. 3, were set at about 0.020 inches gap, and were run at about 5 rpm. The pressure exerted by actuator 42 was about 600 psig. Yield was about 93.8%. From the compactor, the chips were ground in granulator 14, at a rotor speed of about 1500 rpm and then screened in sieve 16, using a 14 mesh screen, U.S. Standard Sieve, to yield about 26 pounds of product having a particle size between about 20 and 80 mesh.

As indicated above, microscopic examination of the recovered material revealed that the needle-like structure was no longer predominant.

Product density increased from an initial density of 0.21 grams per cc to about 0.55 grams per cc. The actual particle size distribution was:

| Sieve Size | Percent Remaining |
|---|---|
| 20 | 15.7 |
| 30 | 20.6 |
| 40 | 13.5 |
| 50 | 11.5 |
| 60 | 2.6 |
| 70 | 4.0 |
| 80 | 2.3 |
| −80 | 29.4 |

Following classification, the product was fed to the fluid bed spray reactor 18 and encapsulated with Durkee 17, referred to above. The aspartame flowed extremely well in the reactor, the particles moving freely and independently, with no evidence of "snowballing". Coating was sprayed on the particles to achieve a coating level of about 15%. The air inlet temperature was about 55° C. (about 130° F.). The loading in the reactor was about 5 kilograms. Nozzle air pressure for the molten stearine was about 4 psig, the nozzle having a port size of about 1.2 millimeters. Stearing flow was about 45 liters per minute.

Following encapsulation, the product from the reactor was employed in a white cake mix formation and compared with a similar formulation employing uncoated aspartame. The formulations were:

| Ingredient | Uncoated Aspartame (grams) | Coated Aspartame (grams) |
|---|---|---|
| maltodextrin | 256 | |
| cake flour | 309 | |
| salt | 7.6 | |
| baking powder | 14 | |
| shortening | 110 | |
| milk | 388 | |
| sweetener | 3 | 3.43 |
| eggs | 110 | |
| vanilla | 6 | |

In the above Table, the only ingredient changed was the sweetener. The use of a larger amount of the coated aspartame (3.43 grams) as compared to only 3 grams of the uncoated aspartame, was necessary to maintain the same level of aspartame in the cake formulation; that is, to compensate for the weight of coating. The use of maltodextrin in the formulation was for the purpose of providing a bulking agent capable of replacing the bulk of sugar in a conventional formulation.

The cakes were baked in 8" pans for 24 minutes at 350° F. The following results were obtained:

TABLE 2

| Ingredient | Percent substrate of APM used | Subjective Comparative Evaluation |
|---|---|---|
| uncoated aspartame | 98.1 | least sweet |
| coated aspartame | 85.8 | much sweeter than uncoated aspartame |

From the above results it was determined that the present invention improves the stability of aspartame through baking to a minimum of about 50% recovery.

It is possible to use ingredients in addition to the substrate and coating material in the practice of the present invention. For instance, it may be desirable to granulate a starch material with the aspartame as a pre-step to encapsulation to increase aspartame particles size, thereby decreasing surface area allowing for equal protection with less coating.

Equally good compaction and granulation results were achieved with niacinamide and ibuprofen.

Although the present invention has been described with reference to the use of melted or molten hydrogenated lipids and waxes, for end applications where water is present, such as baking applications, the invention broadly is useful for other coatings such as water or solvent soluble coatings, in end applications where the same can be used.

We claim:

1. A process for encapsulating materials which are difficult to fluidize in a fluidized bed reactor comprising the steps of
    (1) compacting said materials into a plurality of flat chips;
    (2) grinding said chips into particles having an average particle size in the range of about 20 to about 400 mesh size, U.S. Standard Sieve;
    (3) forming a fluid bed of the particles of step (2) in a fluid bed spray reactor;
    (4) applying a spray of encapsulating coating to the surface of said particles in said reactor, encapsulating said particles;
    (5) withdrawing said encapsulated particles from said reactor.

2. The process of claim 1 wherein said encapsulating coating is a melted or molten hydrogenated lipid or wax.

3. The process of claim 2 wherein said hydrogenated lipid is stearine.

4. The process of claim 1 wherein said difficult to fluidize material is aspartame particles.

5. In an encapsulation process, for the encapsulation of long, needle-like crystalline particles, wherein the encapsulation is carried out in a fluid bed reactor by spray application of an encapsulate onto a fluid bed of such particles, the improvement comprising the steps of, prior to encapsulation,
    compacting said particles into flat sheets;
    breaking said sheets into a plurality of flat chips; and
    granulating said chips into a plurality of small particles having an average particle size within the range of about 20 to about 400 mesh size, U.S. Standard Sieve.

6. Encapsulated particles prepared by the processes of claims 1 or 5.

* * * * *